United States Patent [19]

Komatsu et al.

[11] Patent Number: 5,458,487
[45] Date of Patent: Oct. 17, 1995

[54] SYSTEM FOR ANALYZING OCCLUSION CONDITION

[75] Inventors: Tomoaki Komatsu, Tokyo; Shigeo Sato, Saitama; Makoto Watanabe, Miyagi, all of Japan

[73] Assignee: Fuji Photo Film Co., Ltd., Kanagawa, Japan

[21] Appl. No.: 136,133

[22] Filed: Oct. 15, 1993

[30] Foreign Application Priority Data

Oct. 15, 1992 [JP] Japan ................... 4-302977
Oct. 15, 1992 [JP] Japan ................... 4-302978

[51] Int. Cl.⁶ .................................... A61C 9/00
[52] U.S. Cl. .................................... 433/71; 128/777
[58] Field of Search .................... 433/68, 71; 128/774, 128/776, 777, 778

[56] References Cited

U.S. PATENT DOCUMENTS

| | | | |
|---|---|---|---|
| 3,349,489 | 10/1967 | Shackelford | 433/68 X |
| 3,959,881 | 6/1976 | Kokal, Jr. | |
| 4,390,028 | 6/1983 | Okano et al. | 433/68 X |
| 4,402,326 | 9/1983 | Okano et al. | 128/776 X |
| 4,521,186 | 6/1985 | Wodlinger et al. | 128/777 X |
| 4,547,155 | 10/1985 | Adler | |
| 4,592,727 | 6/1986 | Bloomfield | 433/68 X |
| 4,676,748 | 6/1987 | Pietkivitch | |
| 4,734,034 | 3/1988 | Maness et al. | 433/68 |

FOREIGN PATENT DOCUMENTS

| | | | |
|---|---|---|---|
| 3117248 | 3/1982 | Germany | |
| 1037949 | 2/1989 | Japan | |
| 4099569 | 3/1992 | Japan | |
| 9103980 | 4/1991 | WIPO | 433/68 |

*Primary Examiner*—Nicholas D. Lucchesi
*Attorney, Agent, or Firm*—Sughrue, Mion, Zinn, Macpeak & Seas

[57] ABSTRACT

A system for analyzing the occlusion condition by inspecting an occlusion condition diagnosing sheet including a pressure-sensitive composite recording sheet structure and having at least one surface coated with a wax. The system comprises a first scanner for reading the image of dental arch pattern recorded on the wax, a second scanner for reading the color densities developed on the pressure-sensitive recording sheet structure, an occlusion pressure detector for converting the color densities into pressures, a graduation display device for converting the occlusion pressurs into the density graduations to display the density graduations, and output device for outputting the dental arch pattern and/or distribution of the density graduations.

Further provided is a system for analyzing the occlusion condition by inspecting an occlusion condition diagnosing sheet including a pressure-sensitive composite recording sheet structure. The system comprises a scanner for reading the color density, an occlusion pressure detector for converting the color densities into pressures, a processor for processing the pressures through one or more of plural processings, a mode selector for selecting particular processing mode and output device for outputting the result of processings.

10 Claims, 18 Drawing Sheets

FIG.12
OCCLUSION PRESSURE DISTRIBUTION
[PARTITIONED INTO FOUR PARTS]
[MAXIMUM PRESSURE : 131 Kg/cm²]
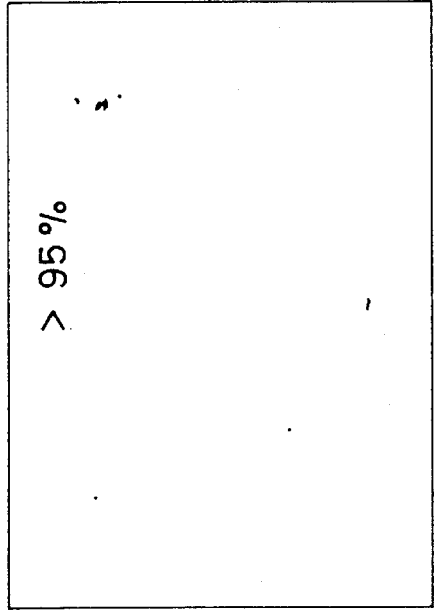
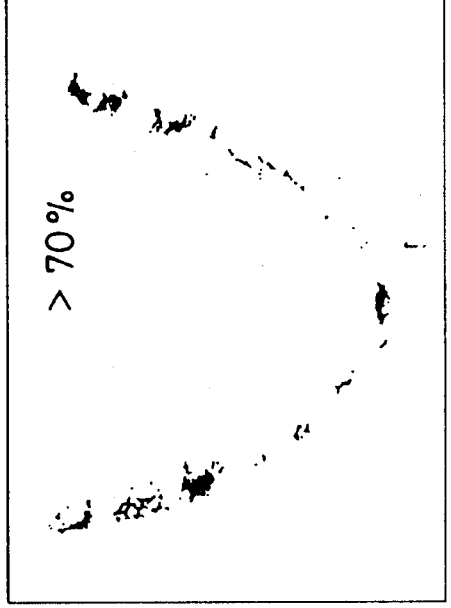
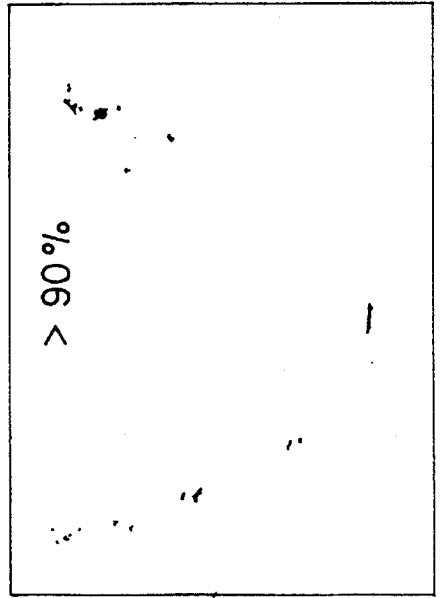
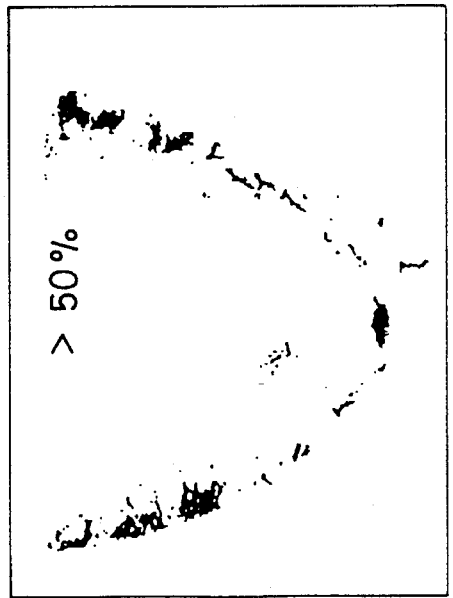

OUTPUT IMAGES SHOWING OCCLUSION PRESSURE BALANCE

OUTPUT IMAGES SHOWING OCCLUSION PRESSURE DISTRIBUTION ALONG XY AXES

RATIO OF $X_1$: 54.1%   RATIO OF $X_2$: 45.9%
RATIO OF $Y_1$: 71.9%   RATIO OF $Y_2$: 28.1%

THREE-DIMENSIONAL PATTERN
OF OCCLUSION PRESSURE

IMAGE SHOWING THE CENTER
OF OCCLUSION PRESSURE
(MEASURED AT X=320, Y=240)

CENTER 11A POSITIONS AT THE POINT
OF X=112, Y=112

FIG.17

OUTPUT IMAGE SHOWING AVERAGE VALUE
OF OCCLUSION PRESSURE LOADING
$\begin{pmatrix} \text{MEASURED AT X=320, Y=240} \\ \text{PITCH AT MEASUREMENT : 0.25 mm} \end{pmatrix}$

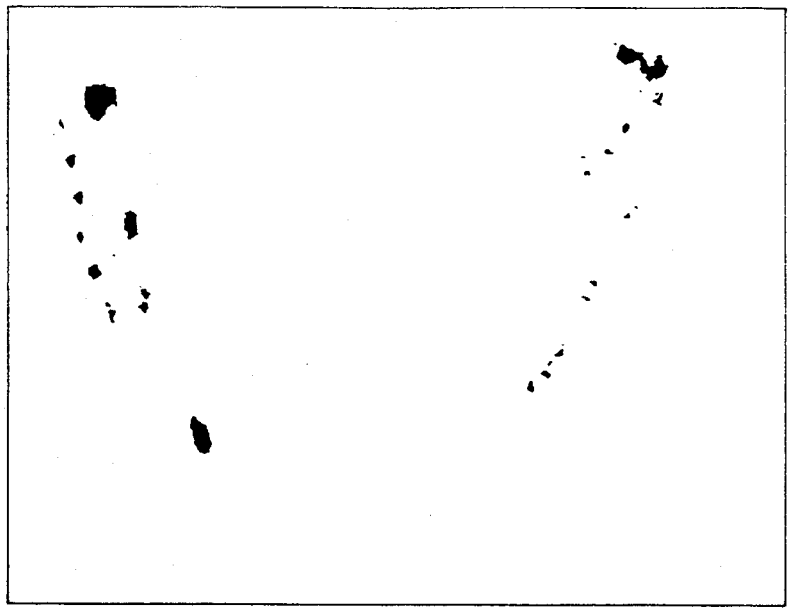

TOTAL LOADING : 22.923 Kg/cm$^2$
AVERAGE OF TOTAL LOADING : 56.51 Kg/cm$^2$
AVERAGE LOADING WITHIN THE RANGE OF
        ABOVE 70 Kg/cm$^2$ : 77.23 Kg/cm$^2$
AVERAGE LOADING WITHIN THE RANGE
        OF 60-70 Kg/cm$^2$ : 64.56 Kg/cm$^2$
AVERAGE LOADING WITHIN THE RANGE
        OF 50-60 Kg/cm$^2$ : 54.87 Kg/cm$^2$
AVERAGE LOADING WITHIN THE RANGE
        OF 40-50 Kg/cm$^2$ : 45.03 Kg/cm$^2$
AVERAGE LOADING WITHIN THE RANGE
        OF 30-40 Kg/cm$^2$ : 34.44 Kg/cm$^2$
AVERAGE LOADING WITHIN THE RANGE OF
        BELOW 30 Kg/cm$^2$ : 27.74 Kg/cm$^2$

FIG.18

OUTPUT DATA SHOWING AREA RATIO
$$\begin{pmatrix} \text{MEASURED AT } X=320, Y=240 \\ \text{PITCH AT MEASUREMENT} : 0.25mm \end{pmatrix}$$

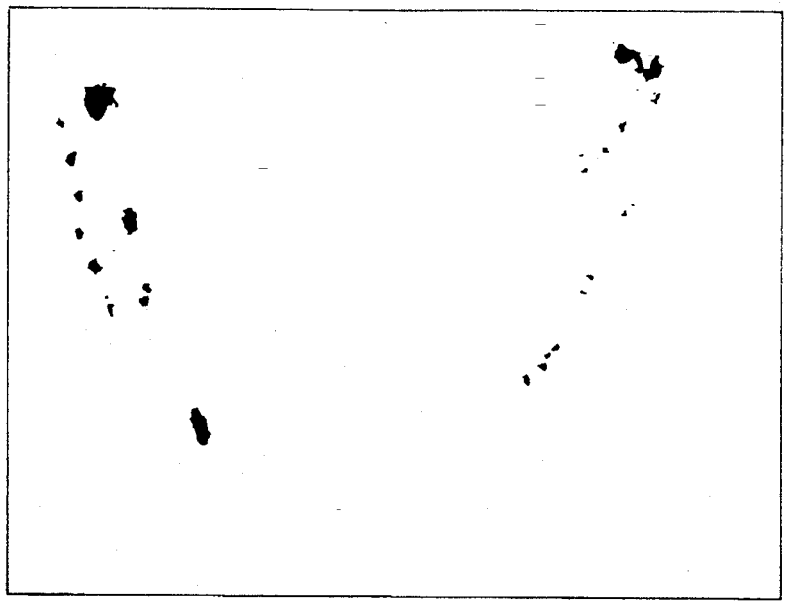

TOTAL AREA APPLIED WITH OCCLUSION PRESSURE
: 0.41 cm$^2$
AREA APPLIED WITH OCCLUSIONAL PRESSURE
OF ABOVE 70Kg/cm$^2$ : 23.11%
AREA APPLIED WITH OCCLUSIONAL PRESSURE
OF 60-70 Kg/cm$^2$ : 20.96%
AREA APPLIED WITH OCCLUSIONAL PRESSURE
OF 50-60 Kg/cm$^2$ : 23.11%
AREA APPLIED WITH OCCLUSIONAL PRESSURE
OF 40-50 Kg/cm$^2$ : 14.18%
AREA APPLIED WITH OCCLUSIONAL PRESSURE
OF 30-40 Kg/cm$^2$ : 13.41%
AREA APPLIED WITH OCCLUSIONAL PRESSURE
OF BELOW 30Kg/cm$^2$ : 5.23%

OUTPUT IMAGE SHOWING NUMERICAL VALUE OF OCCLUSION PRESSURE
(MEASURED AT X=320, Y=240; PITCH AT MEASUREMENT: 0.25 mm)

OUTPUT IMAGE SHOWING NUMERICAL VALUE
OF OCCLUSION PRESSURE $\begin{pmatrix} \text{MEASURED AT X=50, Y=37} \\ \text{PITCH AT MEASUREMENT : 0.25mm} \end{pmatrix}$

SYSTEM FOR ANALYZING OCCLUSION CONDITION

BACKGROUND OF THE INVENTION

1. Field of the Invention

The present invention relates to a system for analyzing the occlusion condition of a patient, wherein an occlusion condition diagnosing sheet including therein a pressure-sensitive composite recording sheet structure is used to inspect the occlusion condition of the patient.

2. Prior Art

In the field of dental treatment, carbon paper has been widely used to determine the occlusion condition of the teeth of a patient. Carbon paper is inserted between the upper and lower dental arches of the patient; and as the patient bites strongly to occlude the upper and lower teeth, carbon particles adhere on the occlusal surfaces at the portions where the upper and lower teeth are abutted. The dentist can diagnose the occlusion condition of the teeth of the patient by observing the positions and areas of the portions to which carbon particles stick.

However, by this prior art of using carbon paper, it is merely possible to detect the portions where the upper and lower teeth abut with each other, and precise detection of occlusion pressure cannot be done by the use of carbon paper. Under such circumstances, the dentist must estimate the occlusion pressure by observing the sticking condition of carbon particles, leading to the problem that the precise diagnosis of occlusion condition of the teeth of the patient cannot be done, leading to difficulty in determination of a subsequent dental treatment course.

Another problem of the prior art, in which carbon paper is used, is that it becomes necessary to impinge the upper and lower teeth plural times or to rub the portions of carbon paper contacting with teeth by the tooth tips, for example, by offsetting the upper and lower jaws and then sliding them laterally.

The prior art technology has another problem that the dentist must precisely position the detecting sheet, such as carbon paper, by looking into the oral cavity of the patient since there is provided no means for precisely positioning the detecting sheet so as to know the portions, at which upper and lower teeth contact or abut with each other. This leads to the problem that the operation efficiency is lowered.

OBJECTS AND SUMMARY OF THE INVENTION

The present invention has been accomplished under the circumstances as aforementioned, and the object thereof is to provide an occlusion pressure detecting system for detecting the tooth alignment condition in the dental arch and the distribution of occlusion pressure of a patient simply and precisely to obtain data which can be used as extremely effective data for the precise diagnosis on the occlusion condition and for the determination of treatment course, by a relatively easier operation for the patient on one hand and on the other hand through a simple operation by the dentist.

According to the invention, the aforementioned object is attained by the provision of a system for analyzing the occlusion condition of a patient by inspecting an occlusion condition diagnosing sheet including a pressure-sensitive composite recording sheet structure and having at least one surface coated with a wax coating layer, comprising:

(a) a first scanner for reading the image of dental arch pattern of the patient, the image being recorded on said wax coating layer;

(b) a second scanner for reading the color densities developed on said pressure-sensitive composite recording sheet structure, the color densities being in proportion to the occlusion pressures applied by respective occluding teeth of the patient;

(c) occlusion pressure detecting means for converting the color densities read by said second scanner into pressures;

(d) graduation display means for converting the detected occlusion pressures into the density graduations to display the thus obtained density graduations; and (e) output means for outputting either one or both of said images of the dental arch of the patient and the distribution of said density graduations of respective occluding teeth.

In a preferred embodiment, the image of the dental arch pattern and the image showing the distribution of the density graduations corresponding to the occlusion pressures are displayed on the output means in the overlapping condition. The system may have a single scanner which is used as the first scanner at any desired time and also used as the second scanner at the time other than the time duration when it is used to serve as the first scanner.

Preferably, the occlusion condition detecting sheet comprises the wax coating layers each having a color different from the color developed on the pressure-sensitive composite recording sheet structure, and more preferably the color of the wax coating layers be complementary to the color developed in the pressure-sensitive composite recording sheet structure so that the colors of the former can be read separately from the color of the latter with ease. In a further preferred embodiment, the color density graduations identifying the occlusion pressures are represented by the varying colors, namely the graduating color densities being stepwisely divided into plural ranges which are represented by a series of varying colors, and the colors identifying the occlusion pressures are displayed on the output means while overlapping with the colored image of the dental arch pattern on each wax coating layer. In a modified embodiment, the output means may be operated alternately to display the image of the dental arch pattern and to display the distribution of the occlusion pressures.

The aforementioned object may also be attained by the provision of a system for analyzing the occlusion condition of a patient by inspecting an occlusion condition diagnosing sheet including a pressure-sensitive composite recording sheet structure having both surfaces sealingly covered with water-impermeable layers, comprising:

(a) a scanner for reading the color density developed on said pressure-sensitive composite recording sheet structure, the color density being in proportion to the occlusion pressure applied by respective occluding teeth of the patient;

(b) an occlusion pressure detector for converting the color densities read by said scanner into pressures;

(c) a processor for processing the pressures through plural sorts of processing;

(d) a mode selector for selecting a particular processing from said plural sorts of processing; and (e) output means for outputting the result of processing carried out under the instruction fed through said mode selector.

It is desirous that said processor operates to find the geometric mean of the occlusion pressures in the dental arch of the patient so that the thus found geometric mean is displayed in the condition of overlapping with the image of the tone graduation of the occlusion pressure distribution.

BRIEF DESCRIPTION OF DRAWINGS

The above and other objects and advantages of the invention will become apparent from the following detailed description of the presently preferred embodiments while referring to the appended drawings, in which

FIG. 12 contains four partitioned diagrams each of which shows an output image obtained at the mode of displaying the occlusion pressure distribution;

FIG. 17 is a diagram showing the output image at the mode of calculating the average value of the occlusion pressure loading;

FIG. 18 is a diagram showing the output image at the mode of calculating the area ratio of the points applied with occlusion pressures;

EMBODIMENTS OF THE INVENTION

First Embodiment

Figure 1:
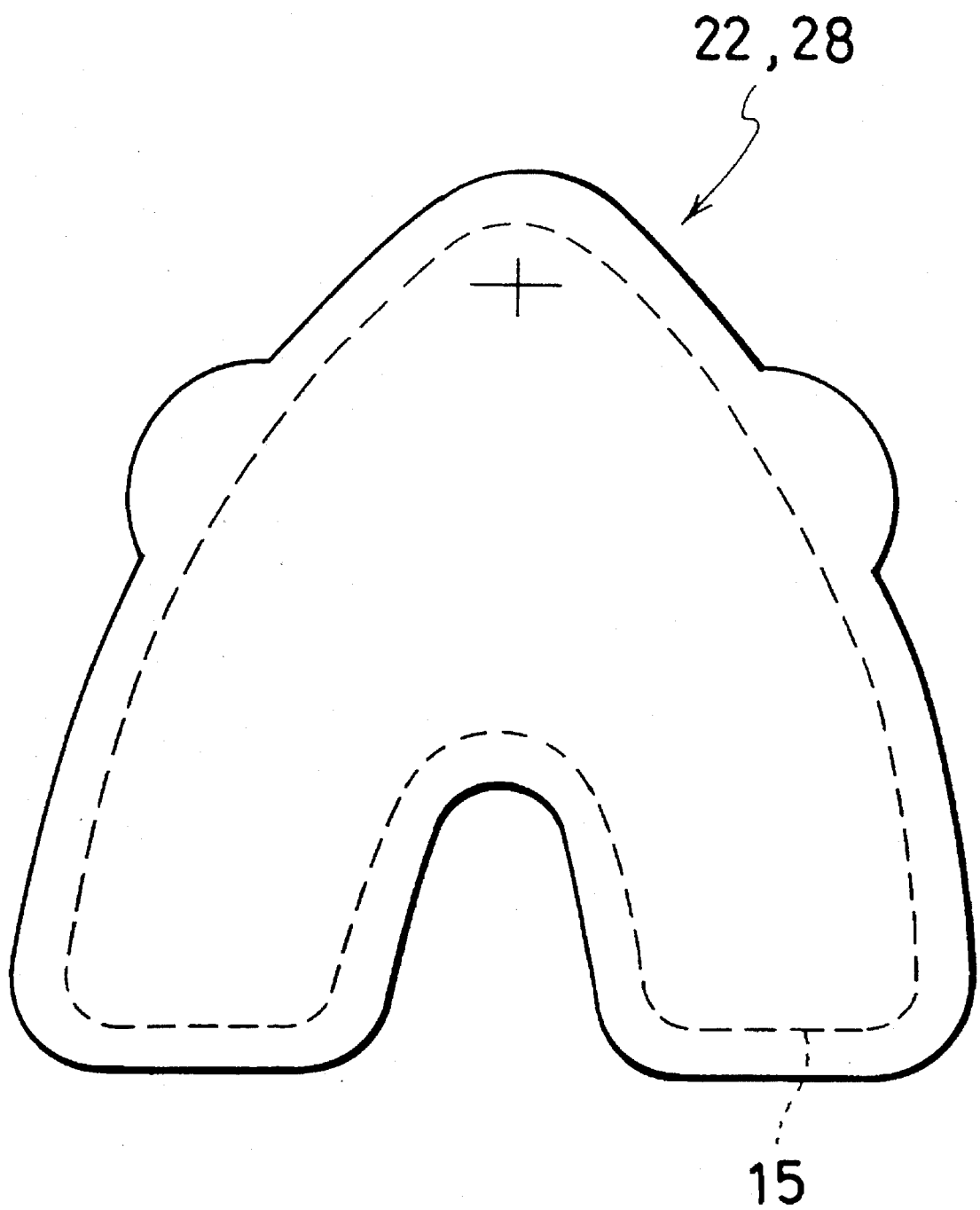
FIG. 1 is a plan view of the occlusion condition diagnosing sheet used in the first embodiment of the invention.
Figure 2:
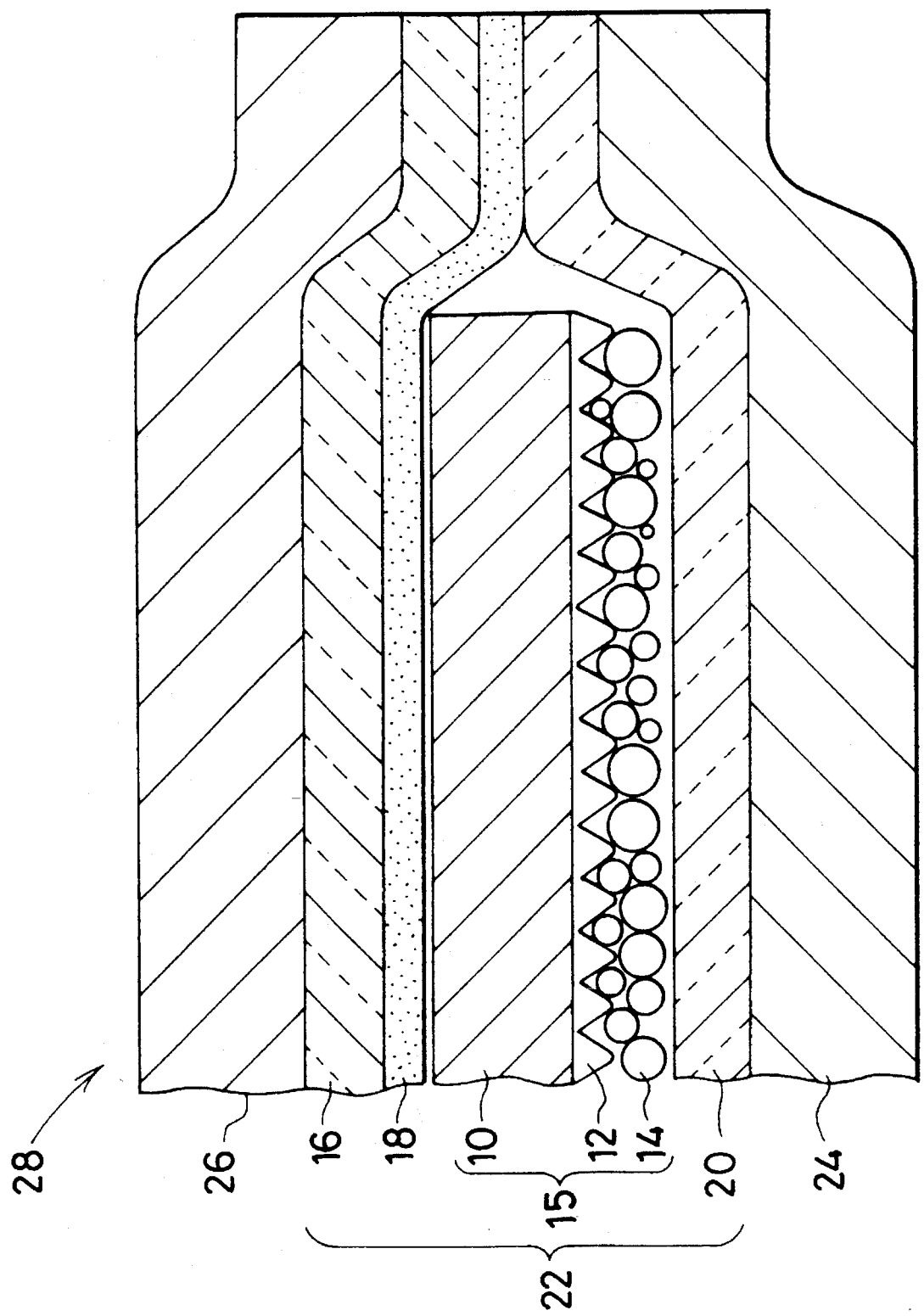
FIG. 2 is a sectional view showing a portion of the occlusion condition diagnosing sheet used in the first embodiment of the invention.
Figure 3:
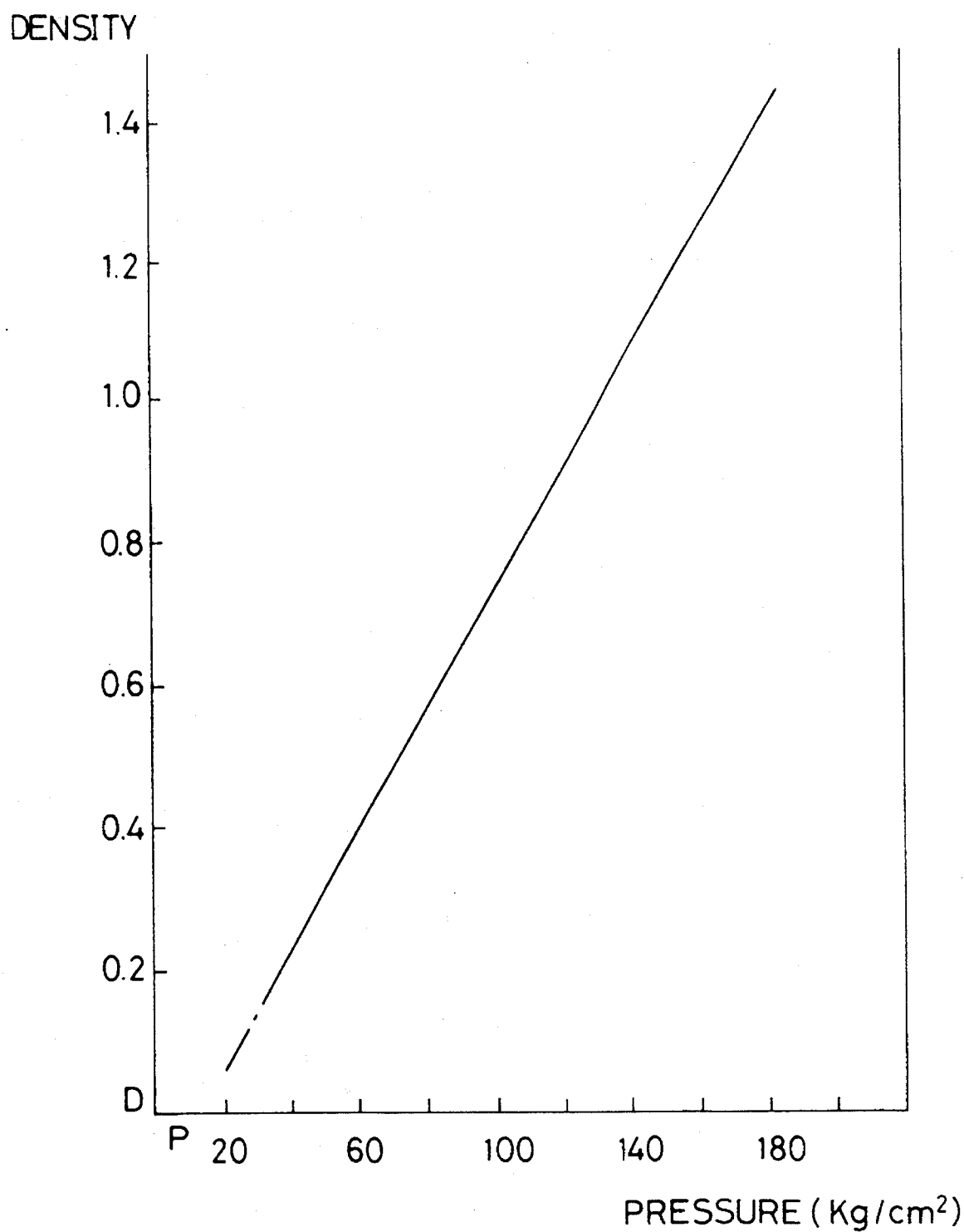
FIG. 3 is a graph showing the interrelation between the applied pressures and the color densities of the pressure-sensitive composite recording sheet structure used in the first and second embodiments of the invention.

FIG. 1 is a plan view of the occlusion condition diagnosing sheet used in the first embodiment of the invention; FIG. 2 is a sectional view showing a portion of the occlusion condition diagnosing sheet used in the first embodiment; and FIG. 3 is a graph showing the interrelation between the applied pressures and the color densities on the pressure-sensitive composite sheet structure used in the first embodiment. In FIG. 2, reference numeral 10 designates a transparent synthetic resin support sheet which is, for example, made of a PET (polyethylene terephthalate) film having a thickness of 25 μm. Reference numeral 12 designates a color developer layer which is formed by coating a dispersion containing montmorillonnite sulfate (obtained by treating acid terra alba (montmorillonnite) with sulfuric acid) in an aqueous sodium hydroxide solution over one face (obverse side) of the support sheet 10, followed by drying.

Reference numeral 14 designates a color former layer overlaid on the color developer layer 12, and is formed by coating a color forming agent, such as 1-phenyl-1-xylylethane, dispersed in an oil in a microcapsulated condition. It is noted hereby that the microcapsules of the color former include microcapsules having varied strengths or resistances to rupture to be ruptured upon application of pressure. As some of the capsules are ruptured, depending on the pressure applied on the recording sheet, the color former contained in the ruptured capsules is absorbed together with the oil by the color developer to develop a color, red in the illustrated embodiment. The density of the thus developed color becomes thicker as the applied pressure is increased. FIG. 3 shows the change in density D of the developed color in terms of the applied pressure P.

More in detail, the pressure-sensitive composite recording sheet used in the invention makes use of coloring upon application of pressure, color development being resulted by the contact between the color former contained in the ruptured microcapsules and the color developer in the color developer layer 12. The microcapsules contained in the color former layer 12 are mixture of a group of microcapsules respectively having different wall thicknesses to be ruptured upon application of different pressures. In other words, the number of capsules ruptured by the application of a particular pressure is intentionally differentiated. As the result of such construction, the density of color, which is developed by the reaction between the color former flowing out of the ruptured capsules and the color developer, developed by the application of a certain pressure is in some proportional interrelationship with the pressure applied on the pressure-sensitive composite recording sheet 15.

The coloring agent is a colorless compound which develops some color upon contact with a solid acid, examples being electron-donating organic compounds. On the other hand, the color developer is a solid acid, more specifically an electron-accepting solid acid. More detailed description of microcapsules, color formers or coloring agents and color developers which may be used in this invention will be found, for example, in Japanese Patent Publication No. 24852/1982 (corresponding to U.S. Pat. No. 4,002,060) and Japanese Patent Publication No. 16654/1984 (corresponding to U.S. Pat. No. 4,132,112). The descriptions in the specifications of these prior Patents will be incorporated herein as the references.

Reference numeral 16 designates a first water-impermeable layer or backside waterproof layer which may be made of a transparent synthetic resin film such as PET film, similar to the film forming the support sheet 10, having a thickness of, for example, 16 μm. A tackifying adhesive is coated on one face, the face opposing to the support sheet 10, of-the first water-impermeable layer 16 to form an adhesive layer 18. Thus, the first water-impermeable layer 16 is liquid-tightly applied on one face (the face opposing to the face to which the color developer layer 12 is applied) of the support sheet 10 through this adhesive layer 18.

Reference numeral 20 designates a second water-impermeable layer or obverse waterproof layer which may be made of a transparent synthetic resin film such as PET film, similar to the film forming the first water-impermeable layer 16, having a thickness of, for example, 16 μm. This second water-impermeable layer 20 is overlaid on the color former layer 14 and has the peripheral margin sealingly adhering to the adhesive layer 18 applied on the first water-impermeable layer 16. It is desirous that the entire marginal portions of both water-impermeable layers 16 and 20 are sealed under a sufficiently reduced pressure.

As should be appreciated by those skilled in the art, the pressure-sensitive recording sheet 22 used in this embodiment is improved in waterproof property and exhibits high reliability in use, since the pressure-sensitive composite recording sheet structure 15 composed of the support sheet 10, the color developer layer 12 and the color former layer 14 is liquid-tightly sealed by means of the first water-impermeable layer 16 and the second water-impermeable layer 20. Moreover, since one of the water-impermeable layer, the first water-impermeable layer 16 in the illustrated embodiment, is closely adhering to the backside of the support sheet 10, the layer 16 is prevented from displacement relative to and delamination from the support sheet 10. With the construction as aforementioned, the second water-impermeable layer 20 is also prevented from relative displacement from the support sheet 10, since the marginal or peripheral portions thereof are fixedly adhering to the marginal or peripheral portions of the first water-impermeable layer 16.

The sheet 22 has a generally horseshoe-like pattern to be fitted with the dental arch of the patient, and has the surfaces coated with wax coating layers 24, 26. Each of the wax coating layers 24, 26 is formed by uniformly coating a dental paraffin wax (JIS-T-6502) to have a thickness of, for example, 0.35±0.3 mm. By coating the wax coating layers 24, 26 on the surfaces of the sheet 22, a finished occlusion condition diagnosing sheet 28 is prepared.

The occlusion condition diagnosing sheet 28 is inserted into the opened mouth of the patient so that it is engaged evenly with the dental arch. As the patient bites the sheet 28 gently, the shapes of teeth in the entire dental arches are recorded as the concaved and convexed traces on these wax coating layers 24, 26. At the same time, the occlusion pressures between the upper and lower occluding teeth are applied on the pressure-sensitive composite recording sheet structure 15 so that the portions on which the pressures are applied are colored, in red in the illustrated example, to have densities varied in proportion to the applied pressures.

Then, the dentist pulls out of the patient's mouth the occlusion condition diagnosing sheet 28 having the wax coating layers 24, 26, on which the dental arch patterns are traced, and including the pressure-sensitive composite sheet structure 15 having portions colored to have color densities in proportion to the applied pressures, and then the sheet 28 is subjected to analysis in the system of the invention. Meantime, in order to facilitate easy and reliable sensing of dental arch patterns and of the occluding pressures, it is desirous that the coloring of the sheet structure 15 is complementary to the color of the wax coating layers 24, 26. For instance, when the color developed in the sheet structure 15 is red, the wax coating layers 24, 26 preferebly have a color close to the color complementary to red, e.g. green or bluish green.

Figure 4:
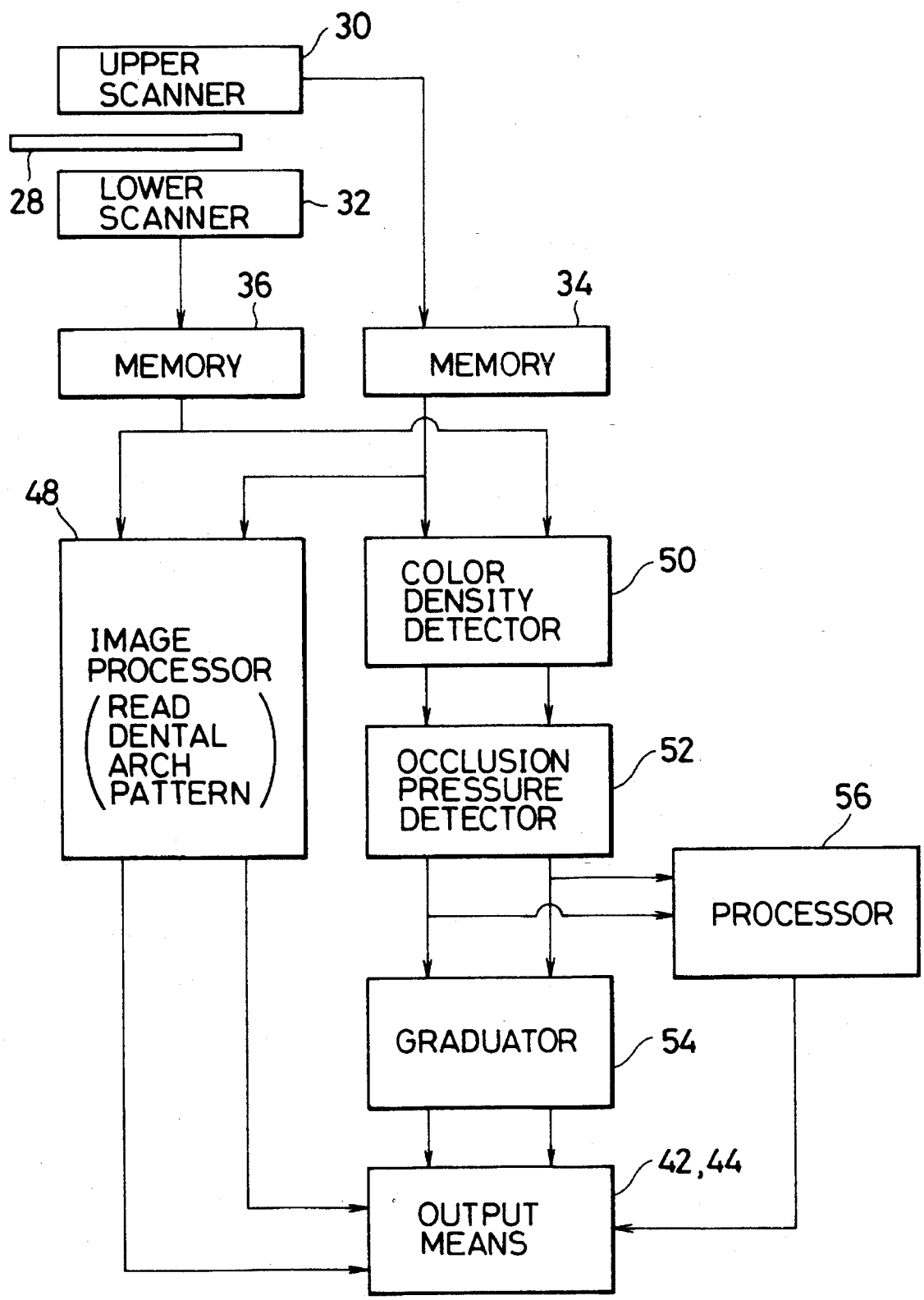
FIG. 4 is a block diagram showing the structure and operation sequence in the first embodiment of the invention.
Figure 5:
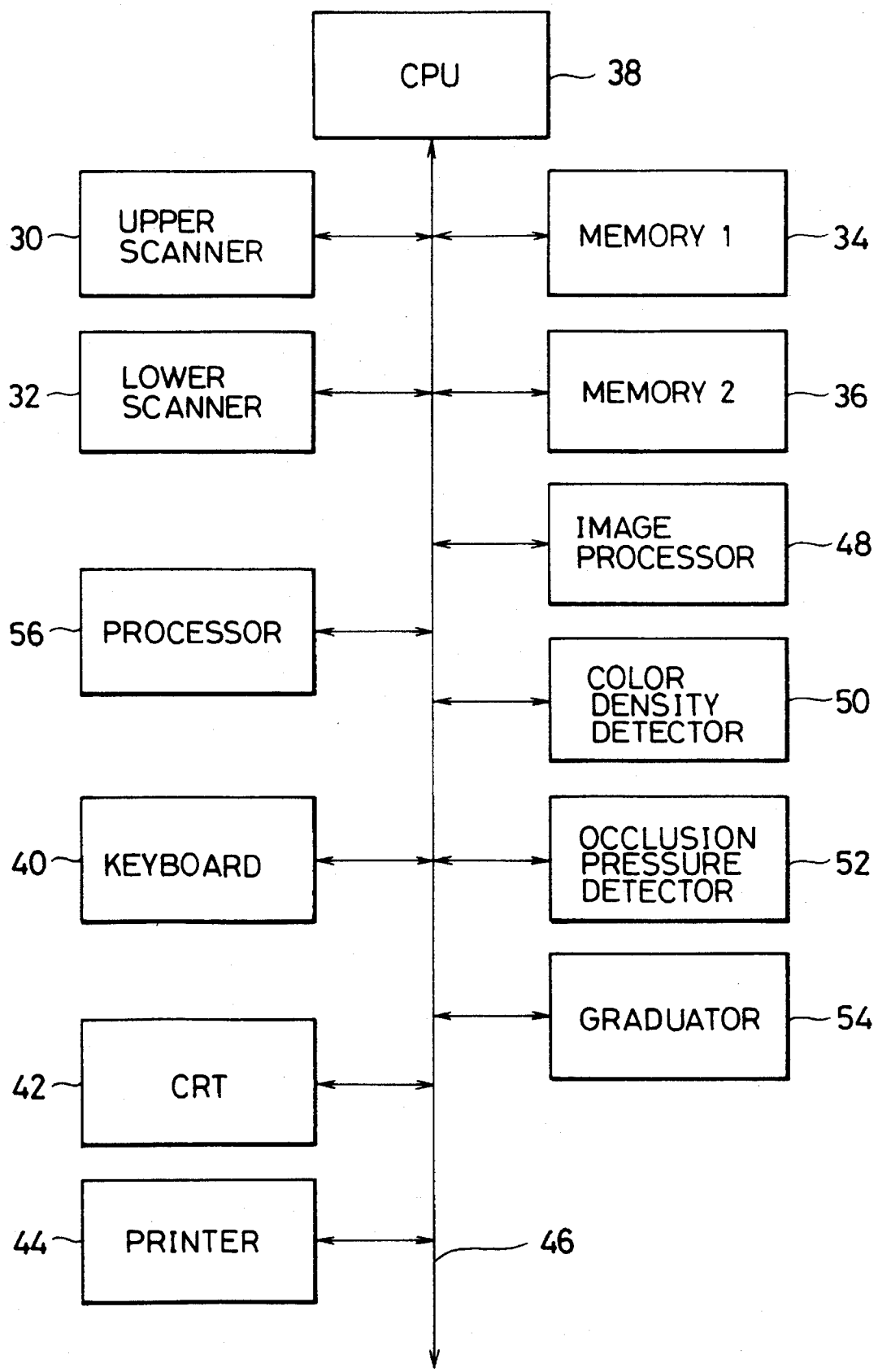
FIG. 5 is a similar block diagram showing the structure and operation sequence in the first embodiment of the invention.
Figure 6:
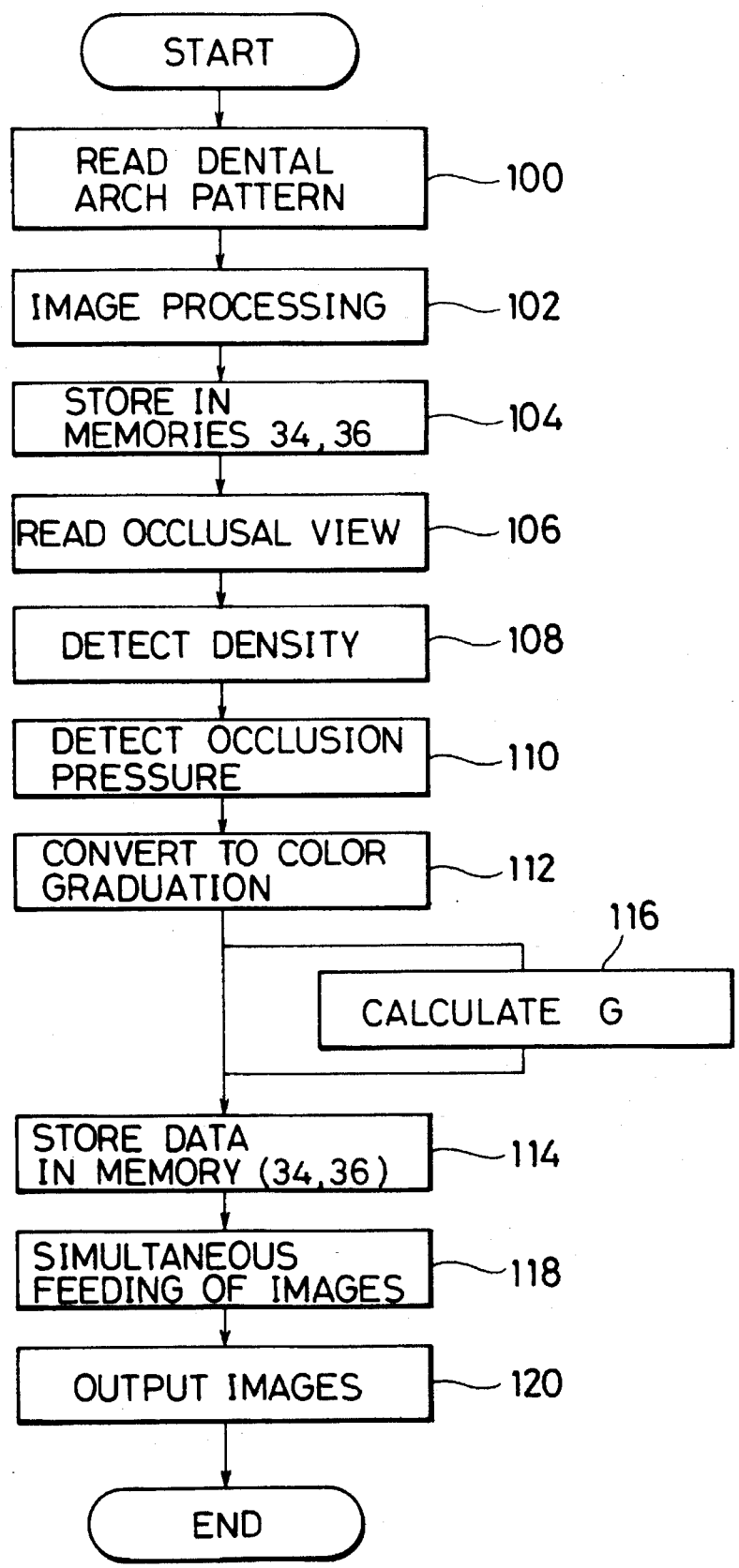
FIG. 6 is a flow chart showing the operation sequence taking place in the system according to the first embodiment.
Figure 7:
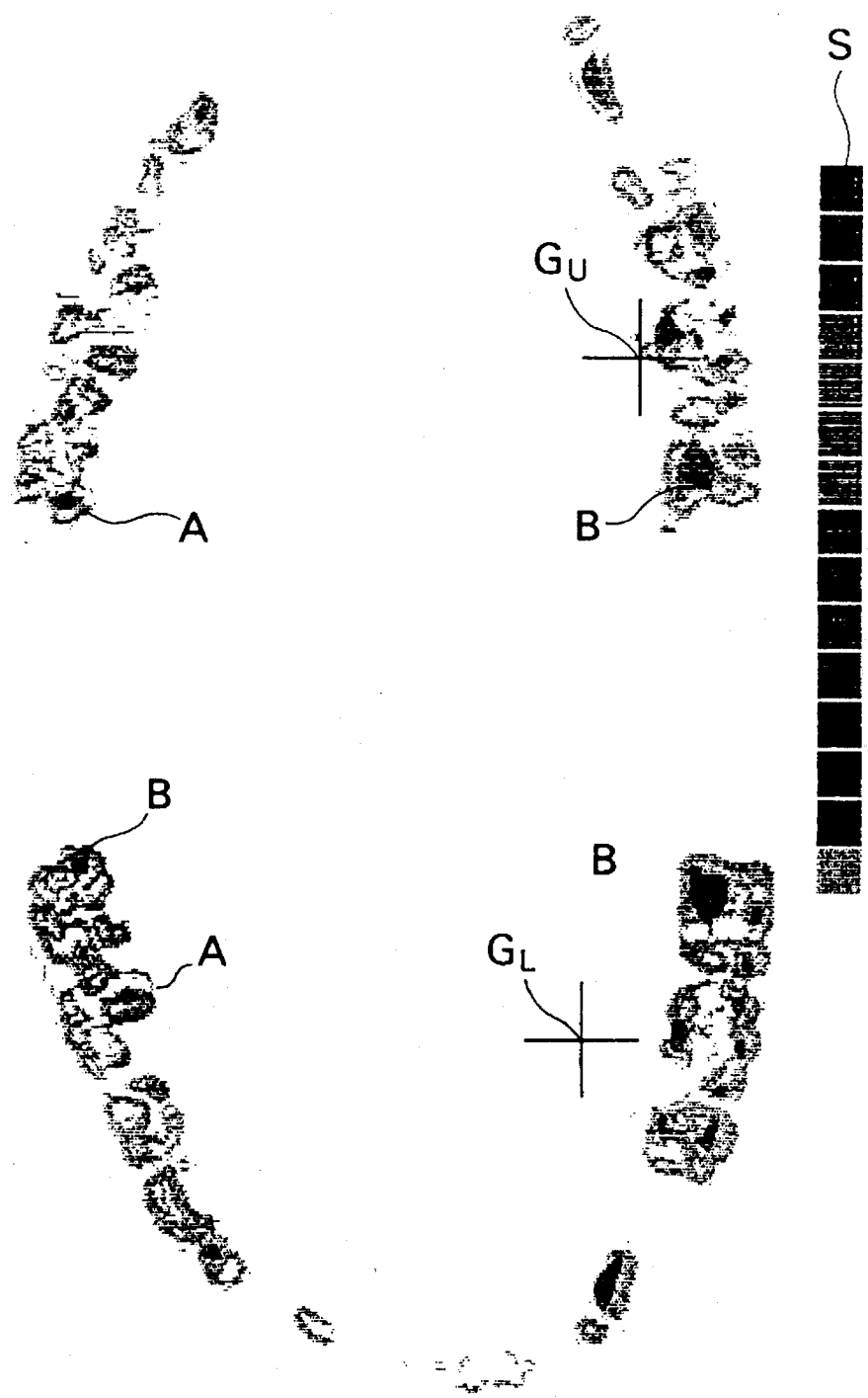
FIG. 7 is a photograph displayed on the output display means of the first embodiment.

FIG. 4 is a block diagram showing the structure and operation sequence in the first embodiment of the invention; FIG. 5 is a similar block diagram showing the structure and operation sequence in the first embodiment of the invention; FIG. 6 is a flow chart showing the operation sequence taking place in the system according to the first embodiment; and FIG. 7 is a photograph displayed on the output display means of the first embodiment.

In FIGS. 4 and 5, reference numeral 30 designates an upper scanner and reference numeral 32 designates a lower scanner. These scanners are color scanners positioned respectively to scan the upper and lower surfaces of the sheet 28 to read the images on the sheet 28.

In the illustrated embodiment, each of the scanners 30, 32 scan the opposing surfaces of the sheet 28 for two times, at one time for reading the concaved and convexed image or trace of the upper or lower dental arch recorded on the wax coating layer 24 or 26, and at the other time for reading the color densities of the image recorded on the pressure-sensitive composite recording sheet structure 15. Namely, each of the scanners 30, 32 serves both as the first scanner for reading the images of dental arch patterns left on the wax coating layers 24, 26 and as the second scanner for reading the color density developed on the pressure-sensitive composite recording sheet structure 15.

Reference numerals 34, 36 designate memories which store the images read by the scanners 30, 32, the processed images or the data obtained through various processings. Referring now to FIG. 5, reference numeral 38 designates a central processing unit (CPU) which is connected to a keyboard 40, a cathode ray tube (CRT) 42 which is used as the output means, and a printer 44 which is also used as the output means. These members are mutually connected through a bus 46. The memories 34, 36 and the scanners 30, 32 are also connected to the bus 46.

Reference numeral 48 designates an image processor by which the images read by the sanners 30, 32 are processed through spatial filtering to be subjected to contour emphasizing, levelling and/or other necessary processings. Reference numeral 50 designates a color density detector for detecting the density of coloring on the pressure-sensitive composite recording sheet structure 15. Reference numeral 52 designates an occlusion pressure detecting means or detector for receiving the outputs, i.e. the color densities D, from the color density detector 50 to determine the value of occlusion pressures P while referring to the curve showing the interrelation between P and D.

Reference numeral 54 designates a graduator, which serves as the graduation display means, for determining the graduations or color ranges for respective occlusion pressure ranges. For example, it is possible to designate specified colors for respective occlusion pressure ranges so that the occluding points, at which the upper and lower lower teeth occlude at different pressures, are represented by different colors.

For instance, in the illustrated example, the pressure ranges are specifically identified as follows:

Pressure range of above 70 kg/cm$^2$: Red

Pressure range of from 60 to 70 kg/cm$^2$: Purple

Pressure range of from 50 to 60 kg/cm$^2$: Blue

Pressure range of from 40 to 50 kg/cm$^2$: Green

Pressure range of from 30 to 40 kg/cm$^2$: Yellow

Pressure range of below 30 kg/cm$^2$: Orange

Reference numeral 56 designates a processor for calculating the center (geometrical mean) of the occlusion pressures. This processor operates to determine the center, i.e. the geometrical mean G, of the occlusion pressures from the distribution of the occlusion pressures detected by the occlusion pressure detector 52.

The operation of the system of this embodiment will now be described with reference to FIG. 6. Initially, the occlusion condition diagnosing sheet 28, which has been bitten by the patient, is set between the upper and lower scanners 30, 32. At the first scanning step, the concaved and convexed images left on the wax coating layers 24, 26 are read by the scanners 30, 32 (Step 100). The images are subjected to contour emphasizing processing and other necessary processings (Step 102), and then stored in the memories 34, 36 (Step 104).

At the second scanning step, the colored image (i.e. the occlusal view) on the pressure-sensitive composite recording sheet structure 15 is read by the scanners 30, 32 (Step 106). Output signals from the scanners 30, 32 are received by the color density detector 50 by which the densities of colored portions are determined (Step 108). The occlusion pressures P corresponding to the densities D, are calculated by the occlusion pressure detector 52 while referring to the curve showing the interrelation between P and D (Step 110).

The thus determined occlusion pressures are converted, respectively, to different colors each corresponding to a specific pressure range by the graduator 54 (Step 112), and the color graduations are stored in the memories 34, 36 (Step 114). The center or geometrical mean G is calculated from the occlusion pressure distribution by the processor 56 (Step 116) and stored in the memories 34, 36 (Step 114).

The images on the wax coating layers 24, 26 and the distribution pattern of the occlusion pressures P determined from the color densities on the sheet 15, both being stored in the memories 34, 36, are simultaneously fed to the output means 42 (CRT in the embodiment shown in FIG. 5) or 44 (a printer in the embodiment shown in FIG. 5) where they are subjected to desired processing to be displayed or printed in the overlapping condition (Steps 118 and 120). As will be seen from FIG. 7 showing the images printed in the overlapping condition, it is convenient that the image or trace of the upper dental arch is displayed in the upper half of the print film and the image of the lower dental arch is displayed in the lower half of the print film, in the condition that the former opposes to the latter.

In FIG. 7, the concaved and convexed images or traces on the wax coating layers 24, 26 are denoted by A and represented, for example, with a light gray color. On the other hand, the occlusion pressures determined from the color densities on the sheet 15 are denoted by B and represented by specific colors which correspond to respective pressure ranges as has been described hereinbefore. Also displayed on the display face of CRT 42 are the point of geometric mean $G_U$ of the upper dental arch and the point of geometric mean $G_L$ of the lower dental arch. The thus displayed images may be output through the printer 44. Further displayed in the right side of the display face is a scale S which shows the interrelation between the ranges of the occlusion pressures and the colors identifying respective ranges.

Although the concaved and convexed traces A on the wax coating layers 24, 26 and the distributions B of the occlusion pressures are displayed in the overlapping condition with each other in the illustrated embodiment, one or more of them may be selectively displayed. For example, only the traces A on the wax coating layers 24, 26 may be displayed to know whether the tooth pattern or alignment is good or bad.

Although the center (geometric mean) G of the occlusion pressures has been calculted in the preceding embodiment, other data may be calculted to be displayed on the display face, such data including, for example, the balance of the occluding pressures between the fore and back teeth, the balance of the occluding pressures between the right and left tooth rows and the balance in area of the occluding teeth.

Since the concaved and convexed dental arch traces recorded on the wax coating layers 24, 26 and the distribution of occlusion pressures recorded on the pressure-sensitive sheet structure 15 can be displayed in the overlapping condition with each other, according to the aforementioned embodiment, the distribution of occlusion pressure can be precisely detected to enable precise diagnosis on the occluding condition thereby to obtain effectual data for the determination of subsequent treating course.

The patient can have diagnosed with each by biting the occlusion pressure diagnosing sheet 28 only one time on one hand, and on the other hand the dentist can readily judge the interrelation between the occluded positions and the occlusion pressures only by observing the occlusion condition diagnosing sheet 28 without the need of watching the oral cavity of the patient.

By displaying the images in the overlapping condition, the positional interrelation between the dental arch traces and the occlusion pressures can be more easily judged. Within the scope of the invention, it suffices to provide only one scanner which is operated as the first scanner at any desired time duration and is also operated as the second scanner at the time duration other than the time when it is used as the first scanner. By differentiating the color developed on the sheet structure 15 used for detecting the occlusion pressure from the color of the wax coating layers 24, 26, particularly the color of the former being substantially complementary to the color of the latter and by properly setting the color selectivities of the scanners, the occlusion pressures can be read separately from the dental arch patterns without the fear of confused reading.

It is convenient that the occlusion pressures are displayed so that they are dividedly represented by different colors such that specific pressure ranges are shown by a series of colors. In such a case, it is also preferable that the colors used for identifying respective pressure ranges are different from the color of the wax coating layers in order to facilitate easy discrimination by the dentist.

Second Embodiment

Figure 8:
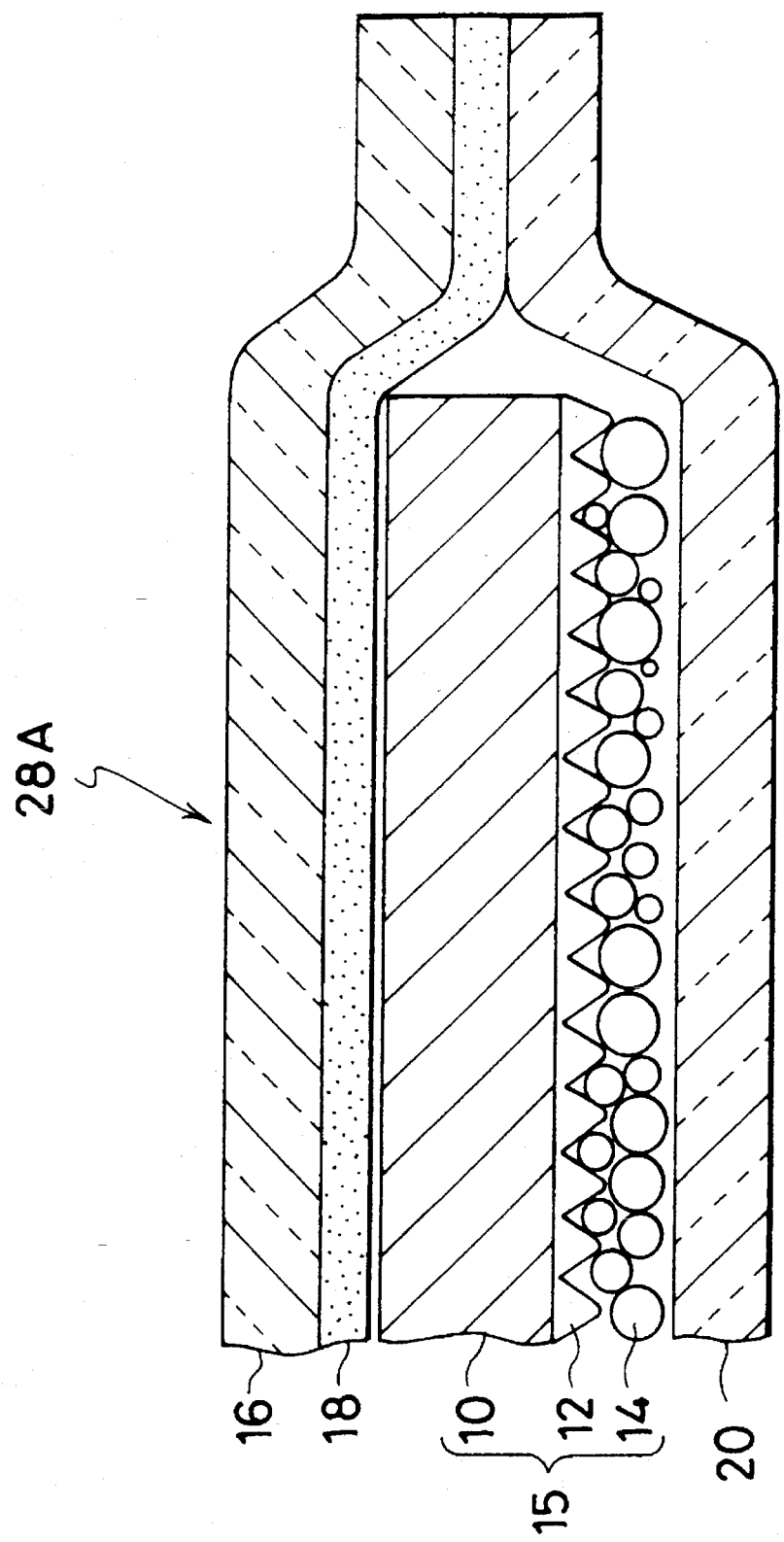
FIG. 8 is a sectional view showing a portion of the occlusion pressure detecting sheet used in the second embodiment of the invention.

FIG. 8 is a sectional view showing the layer structure of an occlusion condition detecting sheet used in a second embodiment of the invention. The shape and structure in the plan view of the sheet is similar to the sheet shown in FIG. 1. In detail, the pressure-sensitive composite recording sheet structure 15 contained within the occlusion condition detecting sheet 28A comprises, similar to that used in the first embodiment, a support 10, a color developer layer 12 coated on one face of the support 10 and a microcapsulated color former layer 14, and has a generally horseshoe-like shape to extend along the arcuated dental arch of human being.

Details of the support 10, the color developer layer 12 and the microcapsulated color former layer 14 are the same as those of the sheet used in the first embodiment, and thus the detailed description thereof will not be repeated here. The change in color density on the pressure-sensitive composite recording sheet structure 15 is also similar to that shown in FIG. 3.

Referring back to FIG. 8, reference numeral 16 designates a first water-impermeable layer or backside waterproof layer which may be made of a transparent PET film, similar to the film forming the support sheet 10, having a thickness of, for example, 16 μ m. A tackifying adhesive is coated on one face, the face opposing to the support sheet 10, of the first water-impermeable layer 16 to form an adhesive layer 18. Thus, the first water-impermeable layer 16 is liquid-tightly applied on one face (the face opposing to the face to which the color developer layer 12 is applied) of the support sheet 10 through this adhesive layer 18.

Reference numeral 20 designates a second water-impermeable layer or obverse waterproof layer which may be made of a transparent PET film, similar to the film forming the first water-impermeable layer 16, having a thickness of, for example, 16 μm. This second water-impermeable layer 20 is overlaid on the color former layer 14 and has the peripheral margin sealingly adhering to the adhesive layer 18 applied on the first water-impermeable layer 16. It is desirous that the marginal portions of both water-impermeable layers 16 and 20 are sealed under a sufficiently reduced pressure.

The generally horseshoe-shaped pressure sensitive composite recording sheet structure 15 is covered with water-impermeable layers 16, 20 with the periphery thereof being sealed through an adhesive layer 18 to the water-impermeable layer 16. Accordingly, the interior of the occlusion condition detecting sheet 28A is liquid-tightly sealed by the first water-impermeable layer 16 and the second water-impermeable layer 20. Thus, the occlusion condition detecting sheet 28A is improved in waterproof property and exhibits high reliability in use, in that coloring property thereof is not affected even if saliva or other aqueous liquids adhere thereto. Moreover, since one of the water-impermeable layer, the first water-impermeable layer 16 in the illustrated embodiment, is closely adhering to the backside of the support sheet 10, the layer 16 is prevented from displacement relative to and delamination from the support sheet 10. With the construction as aforementioned, the second water-impermeable layer 20 is also prevented from relative displacement from the support sheet 10, since the marginal or peripheral portions thereof are fixedly adhering to the marginal or peripheral portions of the first water-impermeable layer 16.

The occlusion condition detecting sheet 28A is inserted into the opened mouth of the patient so that it is engaged evenly with the upper or lower dental arch. As the patient bites the sheet 28A gently, the occlusion pressures between the upper and lower occluding teeth are applied on the pressure-sensitive composite recording sheet structure 15 so that the portions applied with occluding pressures are colored, in red in the illustrated example, to have densities varied in proportion to the applied pressures.

Then, the occlusion condition detecting sheet 28A including the pressure-sensitive composite sheet structure 15 having portions colored to have color densities in proportion to the applied pressures is pulled out of the patient's mouth, and then subjected to analysis in the system of the invention.

Figure 9:
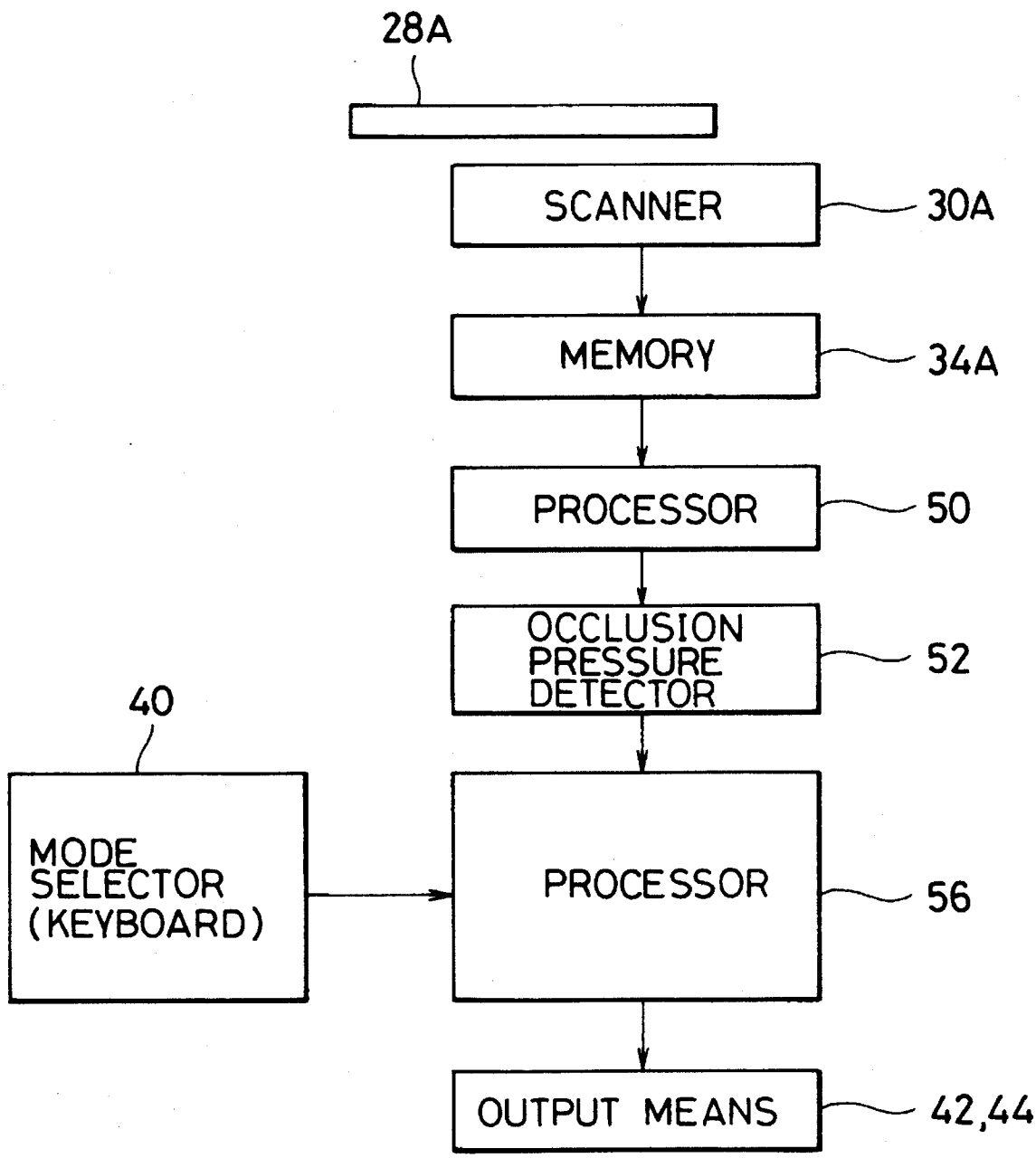
FIG. 9 is a block diagram showing the structure and operation sequence of the second embodiment of the invention.
Figure 10:
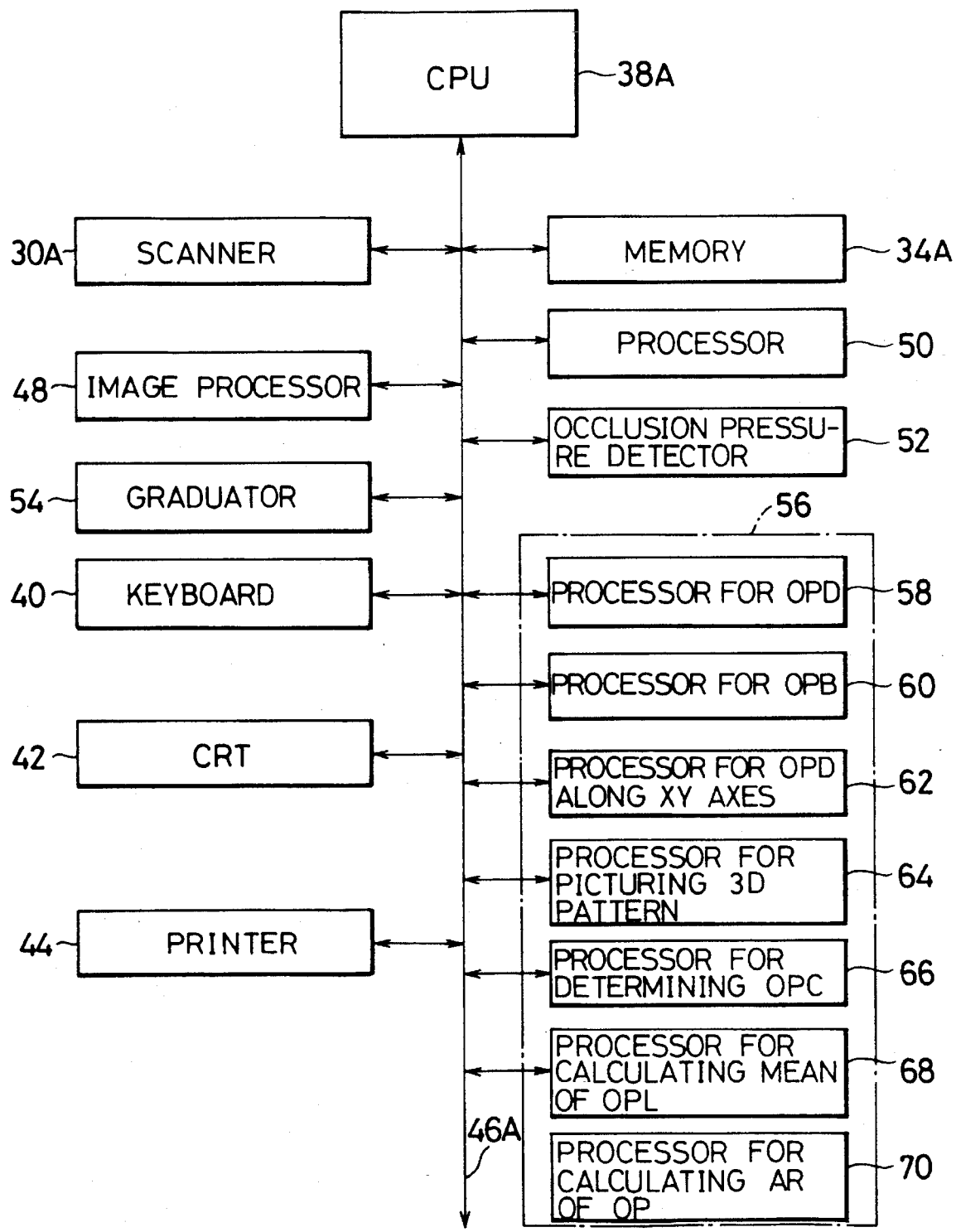
FIG. 10 is a similar block diagram showing the structure and operation sequence of the second embodiment of the invention.
Figure 11:
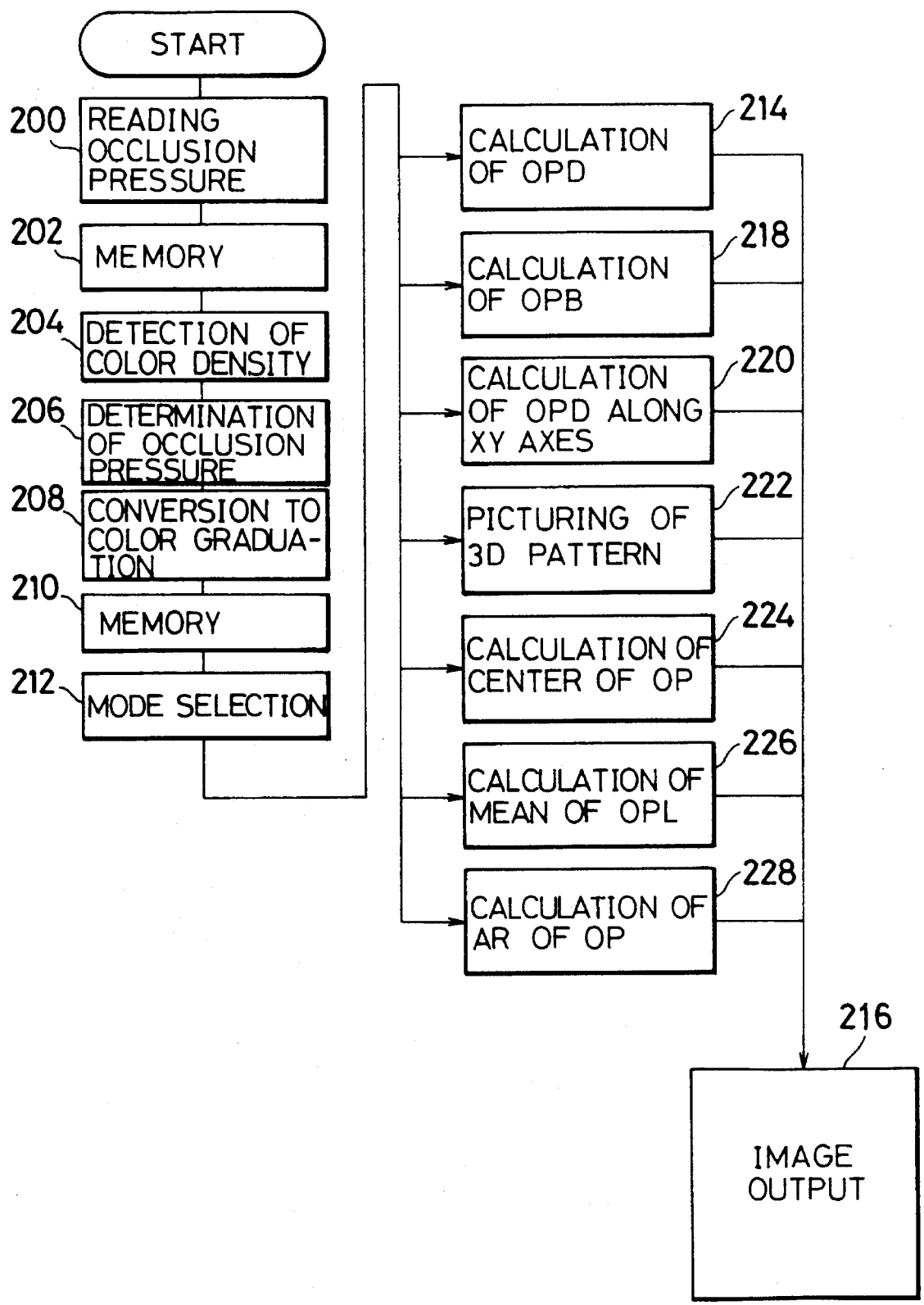
FIG. 11 is a flow chart showing the operation sequence taking place in the system according to the second embodiment.

FIG. 9 is a block diagram showing the structure and operation sequence of the second embodiment of the invention; FIG. 10 is a similar block diagram showing the structure and operation sequence of the second embodiment of the invention; FIG. 11 is a flow chart showing the operation sequence taking place in the system according to the second embodiment; and FIGS. 12 to 20 are photographs or printed matters showing the output images fed from the display or printer means.

Initially referring to FIGS. 9 and 10, reference numeral 30A designates a scanner for reading the colored image on the pressure-sensitive composite recording sheet structure 15 of the occlusion condition detecting sheet 28A from the side of the color former layer 14 (see FIG. 8), and composed of a color scanner in the illustrated embodiment.

Reference numeral 34A designates a memory which stores the images read by the scanner 30A, the processed images or the data obtained through various processings. Referring now to FIG. 10, reference numeral 38A designates a central processing unit (CPU), reference numeral 40 designates a keyboard which may be used also as the selector means, reference numeral 42 designates a cathode ray tube (CRT) which is used as the output means, and reference numeral 44 designates a printer which is also used as the output means. These members are mutually connected through a bus 46A. The memory 34 and the scanner 30 are also connected to the bus 46A.

Reference numeral 48 designates an image processor by which the images read by the sanner 30A are processed through spatial filtering to be subjected to contour emphasizing, levelling and/or other necessary processings. Reference numeral 50 designates a color density detector for detecting the density of coloring on the pressure-sensitive composite recording sheet structure 15. Reference numeral 52 designates an occlusion pressure detecting means for receiving the outputs, i.e. the color densities D, from the color density detecting means 50 to determine the occlusion pressures P while referring to the curve showing the interrelation between P and D.

Reference numeral 54 designates a graduator, which serves as the graduation display means, for determining the graduations or color ranges for respective occlusion pressure ranges. For example, it is possible to designate specified colors for respective occlusion pressure ranges so that the occluding points, at which the upper and lower teeth occlude at different pressures, are represented by different colors.

For instance, in the illustrated example, the pressure ranges are specifically identied as follows:

Pressure range of above 70 kg/cm$^2$: Red

Pressure range of from 60 to 70 kg/cm$^2$: Purple

Pressure range of from 50 to 60 kg/cm$^2$: Blue

Pressure range of from 40 to 50 kg/cm$^2$: Green

Pressure range of from 30 to 40 kg/cm$^2$: Yellow

Pressure range of below 30 kg/cm$^2$: Orange

Reference numeral 56 designates a processor for carrying out a desired operation selected from plural operation programs through the keyboard 40 which serves as the mode selector means. Although the processor 56 is constituted of the CPU 38A in combination with various operation programs, it is denoted in FIG. 10 by plural separate blocks 58 to 70 for respective operation functions in order to facilitate prompt understanding thereof. The contents of these various operations will be described below.

A processor 58 is provided to find the occlusion pressure distribution and to feed the thus found output to the CRT 42 or the printer 44 which gives the displayed images or a print as shown in FIG. 12 (this processor 58 will be referred to as an abridged notation of "Processor for OPD" in FIG. 10). The processor 58 analyzes the detected occlusion pressure distribution to display four separate images selectively in respective quarter parts 7A to 7D, such that the part 7A shows the tooth traces on which occlusion pressures each having a strength of not less than 95% of the maximum occlusion pressure (131 kg/cm$^2$ in the illustrated example) are applied, the part 7B shows the tooth traces on which occlusion pressures each having not less than 90% of the maximum occlusion pressure are applied, the part 7C shows the tooth traces on which occlusion pressures each having not less than 70% of the maximum occlusion pressure are applied, and the part 7D shows the tooth traces on which occlusion pressures each having not less than 50% of the maximum occlusion pressure are applied.

Figure 13:
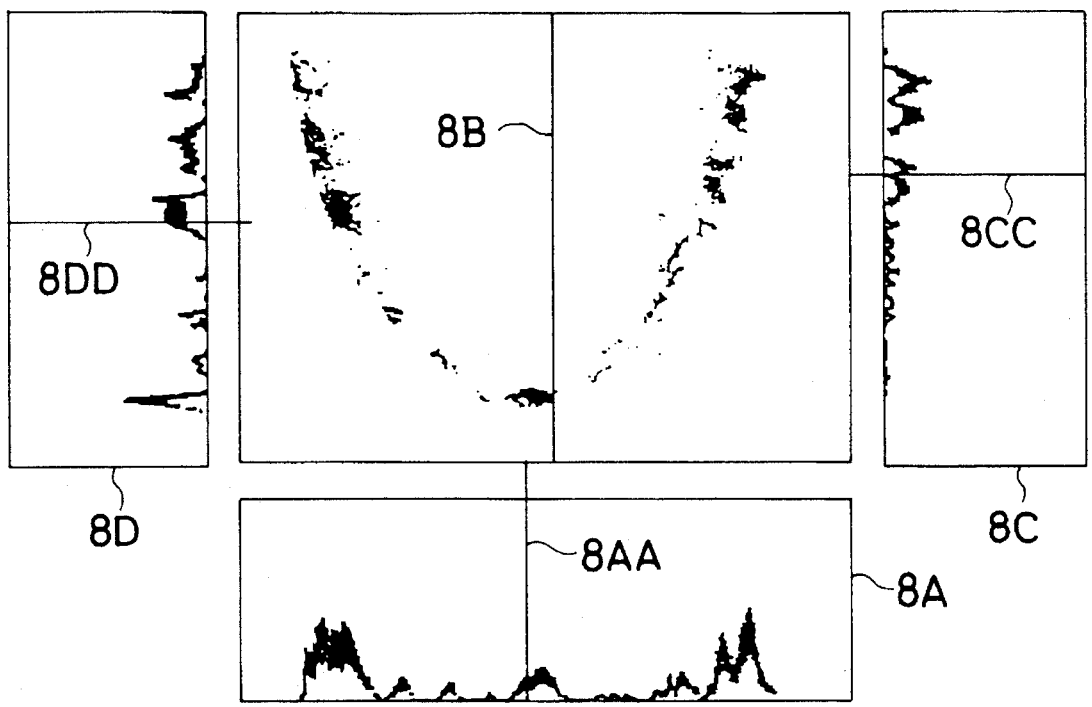
FIG. 13 contains also four partitioned diagrams obtained as the output images at the mode of finding the occlusion pressure balance.

Another processor 60 is provided to find the occlusion pressure balance and to feed the thus found output to the output means 42 or 44 which gives the displayed images or a print as shown in FIG. 13 (this processor 60 will be referred to as an abridged notation of "Processor for OPB" in FIG. 10). The processor 60 operates to find the marginal or peripheral distribution of occlusion pressures by displaying a histogram 8A showing the occlusion pressure distribution in the fore and back tooth rows, a histogram 8C showing the occlusion pressure distribution in the right half of the dental arch and a histogram 8D showing the occulusion pressure distribution in the left half of the dental arch, the dental arch being divided into the right and left halves by the splitting center line 8B. The positions, respectively showing the centers or geometrical means of the applied occlusion pressures, are shown by 8AA, 8CC and 8DD in FIG. 13.

Figure 14:
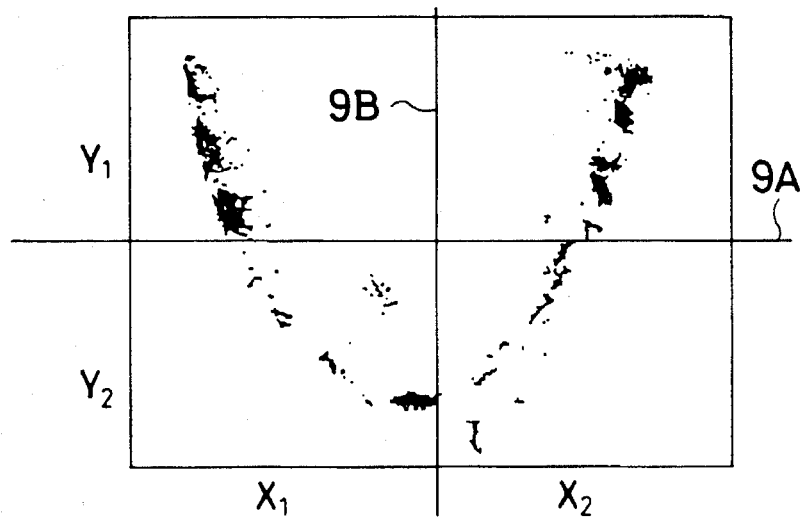
FIG. 14 is a diagram showing the output images at the mode of finding the occlusion pressure distributions along the X and Y axes.

A further processor 62 is provided to find the occlusion pressure distributions along the X and Y axes to feed the output as shown in FIG. 14 (this processor 62 will be referred to as an abridged notation of "Processor for OPD along XY Axes" in FIG. 10). This processor 62 operates to calculate the ratios of the sums of the occlusion pressures within the respective parts $X_1$ and $X_2$, which are divided by the Y axis 9B, relative to the total occlusion pressures; and also operates to calculate the ratios of the sums of the occlusion pressures within the respective parts $Y_1$ and $Y_2$, which are divided by the X axis 9A, relative to the total occlusion pressures, the coordinates axes 9A and 9B being inputted through the keyboard 40. Accordingly, by shifting the coordinates axes 9A and 9B, it becomes possible to draw the axes 9A and 9B by which the ratios of divided occlusion pressures within respective parts occupy 50% of the total occlusion pressures thereby to know the centers (the points giving the geometrical means) of the occlusion pressures along the X and Y axes.

Figure 15:
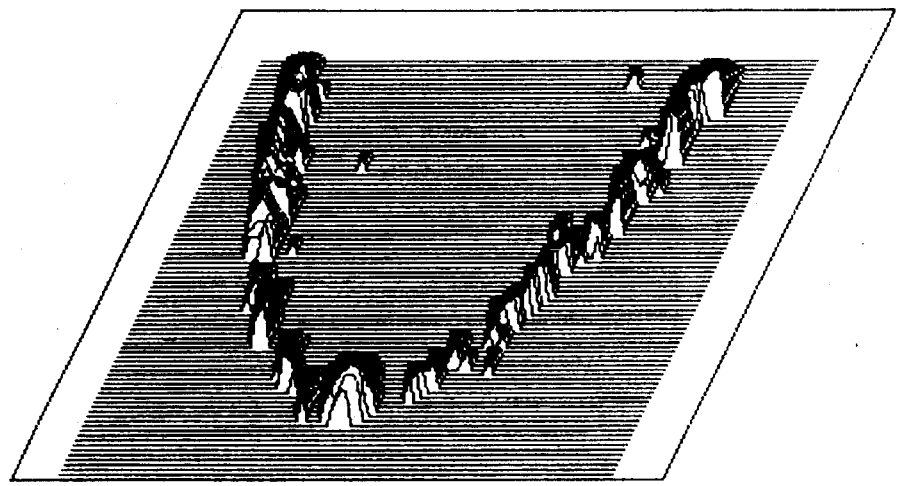
FIG. 15 is a diagram showing the output image at the three-dimensional pattern picturing mode.

A further processor 64 for picturing a three-dimensional pattern of occlusion pressures is provided to output the pattern as shown in FIG. 15 (this processor 64 will be referred to as an abridged notation of "Processor for Picturing 3D Pattern" in FIG. 10). This processor 64 operates to express the occlusion pressure distribution in a three-dimensional sierra form to facilitate prompt grasping of the occlusion pressure distribution.

Figure 16:
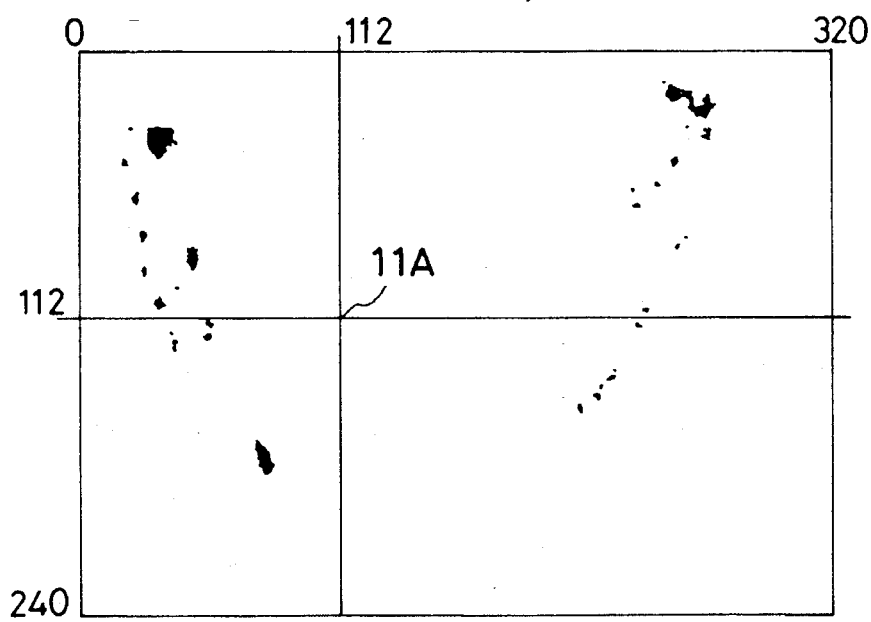
FIG. 16 is a diagram showing the output image at the mode for the determination of the center of occlusion pressures.

A further processor 66 for determining the center of occlusion pressures is provided to output the diagram shown in FIG. 16 in which the center 11A of the occulusion pressure distribution is shown in overlapping condition with the image showing the occlusion pressure distribution (this processor 66 will be referred to as an abridged notation of "Processor for Determining OPC" in FIG. 10). Meanwhile, as will be apparent to those skilled in the art, the center 11A stands for the point of geometrical mean or the center of gravity when the pressures applied on respective occluding points are regarded as if they are gravities.

A still further processor 68 for calculating the mean or average value of the occlusion pressure loading is provided to output the diagram shown in FIG. 17 (this processor 68 will be referred to as an abridged notation of "Processor for Calculating Mean of OPL" in FIG. 10). This processor 68 is provided to know the average values of the occlusion pressures (loadings) within respective ranges. For example, an average pressure or loading is calculated by dividing the sum of occlusion pressures applied on the points contained in a pressure range of from 60 to 70 kg/cm$^2$ by the sum of areas of respective points. In the diagram of FIG. 17, the points on which occlusion pressures within respective ranges are applied are shown with different colors. The used colors are shown in a series of color scale 12A, 12B, 12C, 12D, 12E and 12F in the Figure.

Yet a further processor 70 for calculating the area ratio of the occluding points applied with occlusion pressures is provided to output the diagram of FIG. 18 (this processor 70 will be referred to as an abridged notation of "Processor for Calculating AR of OP" in FIG. 10). This processor 70 operates to calculate the sum of the areas of the occluding points contained in respective pressure ranges, and then the thus calculated sum is divided by the ratio of the areas relative to the total areas of the entire occluding points.

Figure 19:
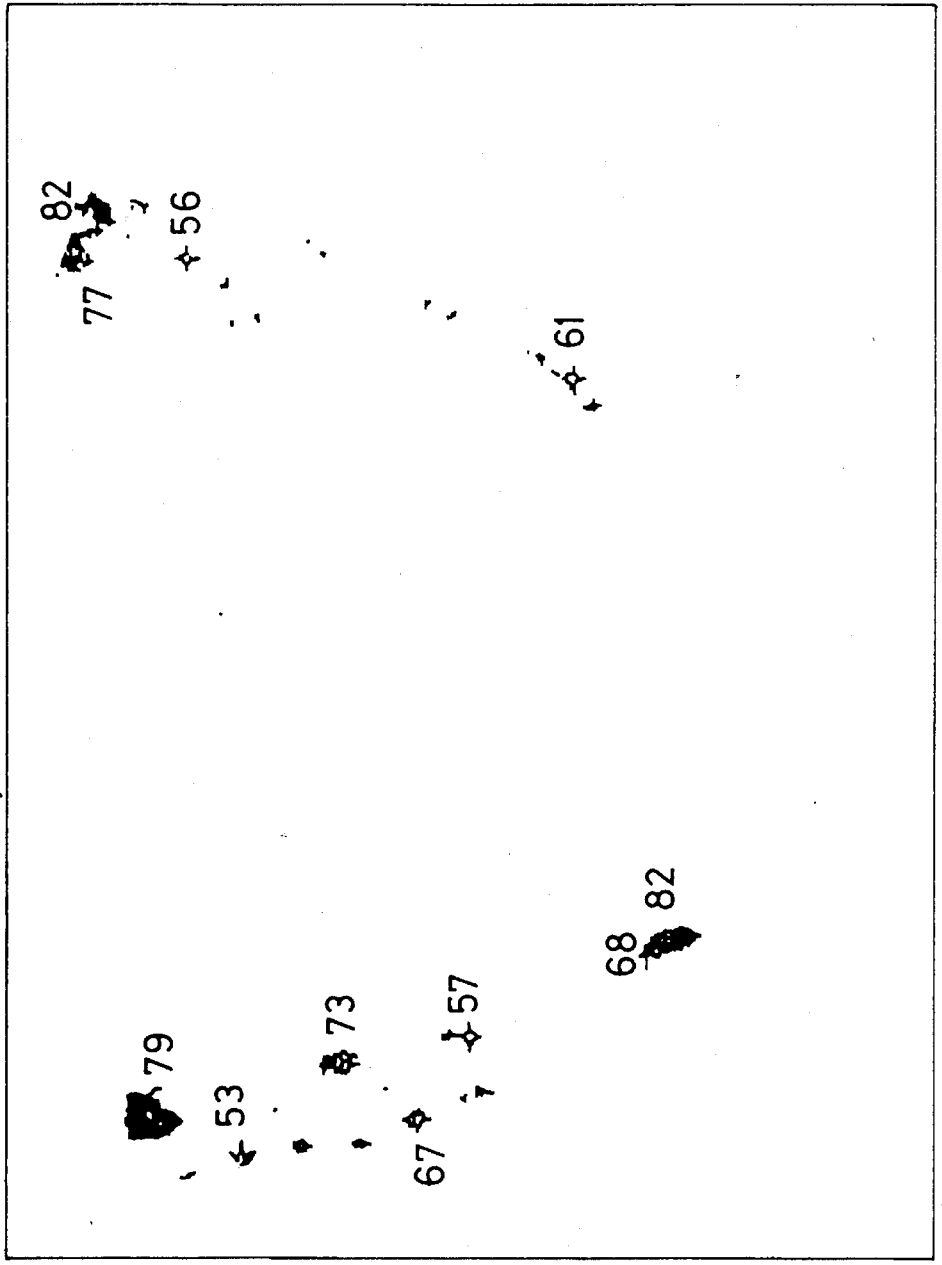
FIG. 19 is a diagram showing the output image at the mode of displaying the numerical values of occlusion pressures.
Figure 20:
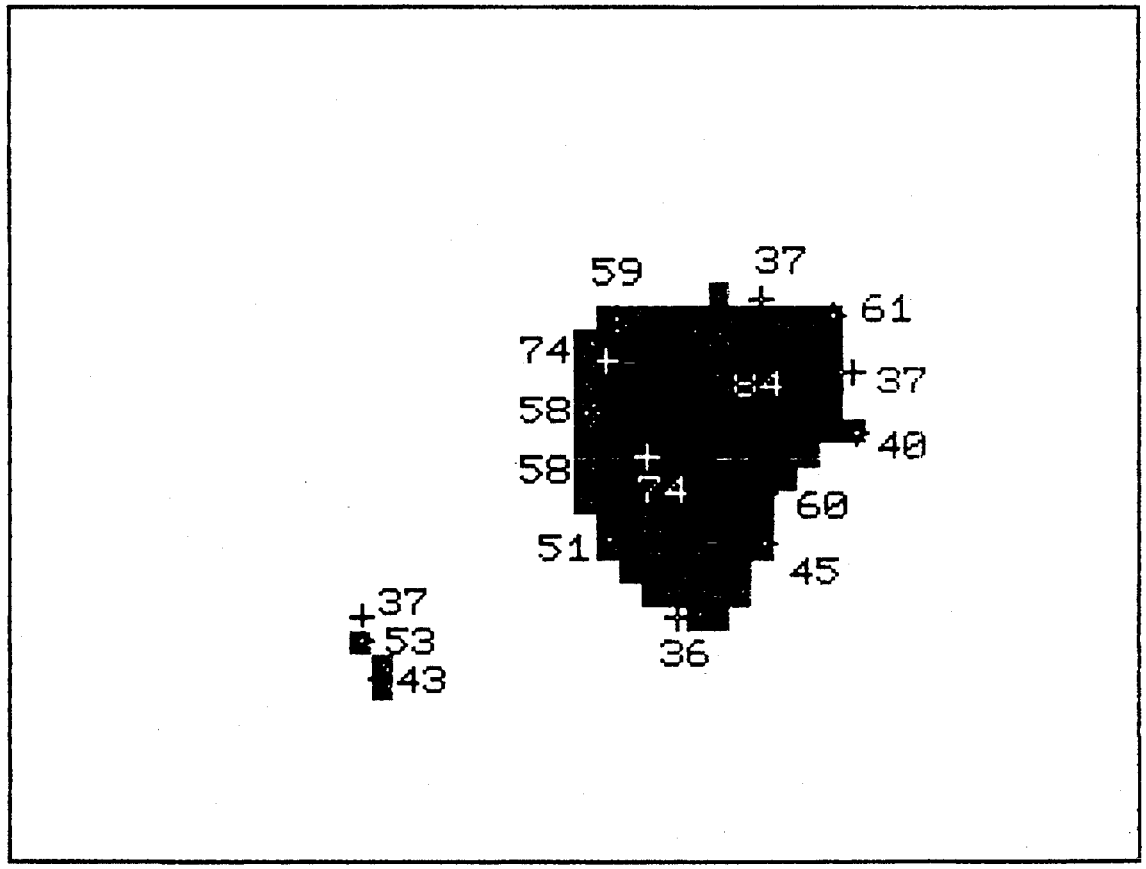
FIG. 20 is a diagram showing the output image at the mode of displaying the occlusion pressure at a certain point in an enlarged condition.

Desired points to be measured may be designated through the keyboard 40 to instruct the processor 56 to feed outputs for displaying the numerical values of occlusion pressures on respective points, as shown in FIGS. 19 and 20. In detail, FIG. 19 shows the numerical values of the occlusion pressures applied on particular measured points, particular measured points being selectively designated, by the keyboard 40, from the points of the dental arch displayed on the CRT 42 in a manner such that the image of dental arch is displayed with different colors depending on the pressure ranges. On the other hand, FIG. 20 shows, in an enlarged scale, the occlusion pressure distribution within a specifically designated area more in detail, the specifically designated area being determined by the instruction through the keyboard 40. By observing the occlusion pressure distribution in the thus enlarged condition, the occlusion or engagement between the upper and lower teeth at the specific point can be inspected in detail.

The operation of the system according to the second embodiment will now be described with reference to FIG. 11. Initially, the occlusion condition detecting sheet 28A, which has been bitten by the patient, is set in the system so that the color former layer side faces to the scanner 30A. The colored image recorded on the pressure-sensitive composite recording sheet structure 15 is thus read through scanning by the scanner 30A (Step 200; Reading of Occlusion Pressure), and then subjected to a proper image processing to be stored in the memory 34A (Step 202).

The densities of the colored images are detected by the color density detector 50 (Step 204; Detection of Occlusion Pressure). The occlusion pressures D corresponding to respective densities P are determined by the occlusion pressure detector 52 in which reference is made to the curve showing the interrelation between P and D (Step 206; Determination of Occlusion Pressure). The thus determined occlusion pressures are converted to colors which is varied, by the graduator 54, correspondingly to the strengths of the applied pressures (Step 208; Conversion to Color Graduation), and then stored in the memory 34A (Step 210).

Then, a processing mode is selected and the selected processing mode is input through the keyboard 40 (Step 212; Mode Selection). When the occlusion pressure distribution calculating mode is selected, the processor 58 operates to carry out necessary processing (Step 214; Calculation of OPD), and the output therefrom is fed to the output means 42 or 44 to give a diagram similar to that shown in FIG. 12 (Step 216; Image Output).

Likewise, by selecting any one of the occlusion pressure balance calculating mode, the mode of calculating the occlusion pressure distribution along X and Y axes, the three-dimensional pattern picturing mode, the mode of finding the center of occlusion pressures, the mode of calculating the average value of occlusion pressure loadings or the mode of calculating the area ratio of occluding points, the corresponding one of the processors 60, 62, 64, 66, 68 or 70 is operated to feed the outputs for displaying one of the images shown in FIGS. 13, 14, 15, 16, 17 and 18 (Step 218, 220, 222, 224, 226 or 228).

Step 218: Calculation of occlusion pressure balance
(Calculation of OPB)
Step 220: Calculation of occlusion pressure distribution along X and Y axes
(Calculation of OPD along XY Axes)
Step 222: Picturing of three-dimensional Pattern
(Picturing of 3D Pattern)
Step 224: Calculation of center of occlusion pressure
(Calculation of Center of OP)
Step 226: Calculation of average value of occlusion pressure loading
(Calculation of Mean of OPL)
Step 228: Calculation of area ratio of occlusion pressure
(Calculation of AR of OP)

It is a matter of course that either one of the modes for displaying the diagrams of FIGS. 19 and 20 may be selected.

According to the second embodiment, since any one or more of plural processings can be carried out by the use of the data relating to the occlusion pressures which are determined from the colored images recorded on the pressure-sensitive composite recording sheet structure, the distribution of occlusion pressures and the occluding conditions at respective points can be precisely detected to enable precise diagnosis on the occluding condition thereby to obtain effectual data for the determination of subsequent treating course.

The patient can have diagnosed with each by biting the occlusion pressure detecting sheet 28A only one time on one hand, and on the other hand the dentist can readily judge the interrelation between the occluded positions and the occlusion pressures only by observing the occlusion pressure detecting sheet 28A without the need of continuous watching of the oral cavity of the patient. As an additional merit, not only the dentist but also the patient can know the occluding condition of teeth by himself or herself.

By selecting the mode for calculating the center of occlusion pressures through the processor and by displaying the thus calculated center of occlusion pressures and the occlusion pressure distribution in the overlapping condition with each other, more precise diagnosis on the occluding condition can be rendered.

What is claimed is:

1. A system for analyzing an occlusion condition of a patient by inspecting an occlusion condition diagnosing sheet including a pressure-sensitive composite recording sheet structure and having at least one surface coated with a wax coating layer, comprising:

(a) a first scanner for reading an image of a dental arch pattern of the patient, the image being recorded on said wax coating layer;

(b) a second scanner for reading color densities developed on said pressure-sensitive composite recording sheet structure, the color densities being in proportion to occlusion pressures applied by respective occluding teeth of the patient;

(c) occlusion pressure detecting means for converting the color densities read by said second scanner into occlusion pressures;

(d) graduation display means for converting the detected occlusion pressures into density graduations to display the thus obtained density graduations; and (e) output means for outputting either one or both of said image of the dental arch of the patient and a distribution of said density graduations of respective occluding teeth.

2. The system of claim 1, wherein said output means comprises display means and wherein said image of the dental arch of the patient and the distribution of said density graduations of respective occluding teeth are displayed on said display means in an overlapping condition.

3. The system of claim 1, wherein said wax coating layer has a first color differentiated from a second color developed on said pressure-sensitive composite recording sheet structure, and wherein said first scanner selectively senses the first color of said wax coating layer and said second scanner selectively senses the second color developed on said pressure-sensitive composite recording sheet structure.

4. The system of claim 1, wherein said graduation display means displays a change in occlusion pressure in terms of the change in color tone.

5. The system of claim 1, wherein said output means comprises a printer which prints out a printed image.

6. The system of claim 1, wherein said output means comprises display means for displaying the image of said dental arch pattern in a certain color and for displaying the occlusion pressures in color tones different from said certain color used for displaying said image of the dental arch.

7. A system for analyzing an occlusion condition of a patient by inspecting an occlusion condition diagnosing sheet including a pressure-sensitive composite recording sheet structure having both surfaces sealingly covered with water-impermeable layers, comprising:

(a) a scanner for reading color densities developed on said pressure-sensitive composite recording sheet structure, the color densities being in proportion to occlusion pressures applied by respective occluding teeth of the patient;

(b) an occlusion pressure detector for converting the color densities read by said scanner into occlusion pressures;

(c) a processor for processing the occlusion pressures through plural sorts of processing and outputting results of operation processing;

(d) a mode selecting means for selecting a particular processing from said plural sorts of processing in response to a received instruction; and (e) an output means for outputting the results of operation processing received from the processor.

8. The system of claim 7, further comprising:

(f) graduation display means for converting the occlusion pressures detected by said occlusion pressure detector into density graduations to display the thus obtained density graduations; and wherein said output means comprises display means for displaying a distribution of said density graduations of respective occluding teeth together with the results of operation processing carried out by said processor.

9. The system of claim 7, wherein said processor operates to find a geometric mean of the occlusion pressures in a dental arch of the patient.

10. A system for analyzing an occlusion condition of a patient by inspecting an occlusion condition diagnosing sheet including a pressure-sensitive composite recording sheet structure and having at least one surface coated with a wax coating layer comprising:

a scanner for reading an image of a dental arch pattern of the patient, the image being recorded on said wax coating layer, and for reading color densities developed on said pressure-sensitive composite recording sheet structure, the color densities being in proportion to occlusion pressures applied by respective occluding teeth of the patient;

occlusion pressure detecting means for converting the color densities read by said scanner into occlusion pressures;

graduation display means for converting the detected occlusion pressures into density graduations to display the thus obtained density graduations; and output means for outputting either one or both of said image of the dental arch of the patient and a distribution of said density graduations of respective occluding teeth.

* * * * *